(12) United States Patent
Mansfield

(10) Patent No.: US 7,848,488 B2
(45) Date of Patent: Dec. 7, 2010

(54) RADIATION SYSTEMS HAVING TILTABLE GANTRY

(75) Inventor: Stanley Mansfield, Sunnyvale, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 122 days.

(21) Appl. No.: 11/852,432

(22) Filed: Sep. 10, 2007

(65) Prior Publication Data
US 2009/0067579 A1 Mar. 12, 2009

(51) Int. Cl.
*A61N 5/10* (2006.01)
*H01J 31/49* (2006.01)

(52) U.S. Cl. .......................................... 378/65; 378/197

(58) Field of Classification Search .................... 378/11, 378/15, 17, 65, 189, 197, 20, 208
See application file for complete search history.

(56) References Cited

U.S. PATENT DOCUMENTS

| | | | |
|---|---|---|---|
| 6,800,858 B1 | 10/2004 | Seppi | |
| 6,888,919 B2 | 5/2005 | Graf | |
| 6,969,194 B1* | 11/2005 | Nafstadius | 378/197 |
| 7,054,410 B2 | 5/2006 | Zentai et al. | |
| 7,085,347 B2* | 8/2006 | Mihara et al. | 378/65 |
| 7,095,028 B2 | 8/2006 | Mollov et al. | |
| 2005/0082491 A1 | 4/2005 | Seppi et al. | |
| 2005/0084073 A1 | 4/2005 | Seppi et al. | |
| 2007/0003021 A1 | 1/2007 | Guertin et al. | |
| 2008/0240363 A1* | 10/2008 | Grebner et al. | 378/198 |

* cited by examiner

*Primary Examiner*—Irakli Kiknadze
(74) *Attorney, Agent, or Firm*—Vista IP Law Group, LLP.

(57) ABSTRACT

A radiation system includes a gantry having an opening and a first axis associated with the opening, a radiation source coupled to the gantry, a first bearing located adjacent a left side of the gantry, and a second bearing located adjacent a right side of the gantry, wherein the gantry is tiltable about the first and second bearings, the first and second bearings forming a second axis that is at a first angle relative to the first axis. A radiation system includes a gantry having an opening and a first axis associated with the opening, a radiation source coupled to the gantry, and a base to which the gantry is rotatably coupled, wherein the gantry is tiltable relative to the base about a second axis that forms an angle relative to the first axis, wherein an uppermost portion of the gantry is not coupled to a support frame of the gantry.

42 Claims, 7 Drawing Sheets

RADIATION SYSTEMS HAVING TILTABLE GANTRY

FIELD

This application relates generally to radiation systems, and more specifically, to radiation systems having treatment and/or diagnostic capability.

BACKGROUND

Radiation therapy involves medical procedures that selectively expose certain areas of a human body, such as cancerous tumors, to doses of radiation. The purpose of the radiation therapy is to irradiate the targeted biological tissue such that undesirable tissue is destroyed. Radiation has also been used to obtain images of tissues for planning or treatment purposes.

During a radiation planning session, radiation treatment planning is performed before treatment radiation is delivered to a patient. This allows an accurate and precise dosage of radiation to be delivered to a patient. During the planning session, configuration data, such as location, size, and shape of a target object, may be acquired from an imaging procedure. Such imaging procedure may be performed using existing CT imaging systems. Existing CT imaging systems are configured to take image slices of the patient in which the image slices are vertical (or perpendicular to a longitudinal axis of the patient or patient support). However, in some cases, it may be desirable to take image slices that are non-vertical or non-perpendicular to the longitudinal axis of the patient or the patient support. Another problem associated with existing imaging systems is that use of such systems generally requires the patient to be supported and oriented horizontally. However, in some cases, a patient may not feel comfortable resting horizontally (as in the case with emphysema patients), or may not physically lay flat horizontally due to an injury or illness.

After the radiation treatment plan is determined, the patient then undergoes a radiation treatment procedure. During a radiation treatment procedure, a radiation treatment system is used to deliver a desired radiation dosage to the patient according to the determined radiation treatment plan. In existing radiation treatment systems, the radiation source that generates the radiation beam is configured to rotate within a plane that is substantially vertical (or perpendicular to a longitudinal axis of the patient or the patient support). Varying the intensity and the entry angle of the incident radiation beam allows a radiation specialist to generate a radiation dose volume that corresponds to the size, shape, and location of the target region. However, in some cases, it may be desirable to deliver radiation beams that do not lie within a vertical plane. Also, it may be desirable to deliver radiation beams that lie in a plurality of planes (which may or may not include a vertical plane). Further, as in the case with the imaging procedure, in the treatment procedure, a patient may not feel comfortable resting horizontally (as in the case with emphysema patients), or may not physically lay flat horizontally due to an injury or illness.

SUMMARY

In accordance with some embodiments, A radiation system includes a gantry having an opening and a first axis associated with the opening, the opening having a width that is at least 24 inches, a radiation source coupled to the gantry, a first shaft located adjacent a left side of the gantry, and a second shaft located adjacent a right side of the gantry, wherein the gantry is tiltable about the first and second shafts, the first and second shafts forming a second axis that is at a first angle relative to the first axis.

In accordance with other embodiments, a radiation system includes a gantry having an opening and a first axis associated with the opening, the opening having a width that is at least 24 inches, a radiation source coupled to the gantry, and a base to which the gantry is rotatably coupled, wherein the gantry is tiltable relative to the base about a second axis that forms an angle relative to the first axis, wherein an uppermost portion of the gantry is not coupled to a support frame of the gantry.

In accordance with other embodiments, a radiation system includes a gantry having an opening and a first axis associated with the opening, a treatment radiation source coupled to the gantry, a diagnostic radiation source coupled to the gantry, and an imager in operative position relative to the diagnostic radiation source, wherein the treatment radiation source is tiltable about a second axis that forms a first angle relative to the first axis.

In accordance with other embodiments, a method of executing a treatment plan includes receiving a treatment plan, and executing the treatment plan by tilting a structure that carries a radiation source, wherein the structure is tilted relative to a floor about a first axis that forms a first angle with a substantially horizontal axis.

In accordance with other embodiments, a computer product includes a computer-readable medium, the computer-readable medium having a set of stored instructions, an execution of which causes a process to be performed, the process comprising receiving a treatment plan, and executing the treatment plan by sending a signal to cause a tilting of a structure that carries a radiation source, wherein the structure is tilted relative to a floor about a first axis that forms a first angle with a substantially horizontal axis.

Other aspects and features will be evident from reading the following detailed description of the embodiments.

BRIEF DESCRIPTION OF THE DRAWINGS

The drawings illustrate the design and utility of preferred embodiments, in which similar elements are referred to by common reference numerals. In order to better appreciate how advantages and objects of the embodiments are obtained, a more particular description of the embodiments will be illustrated in the accompanying drawings.

DETAILED DESCRIPTION OF THE EMBODIMENTS

Figure 1:
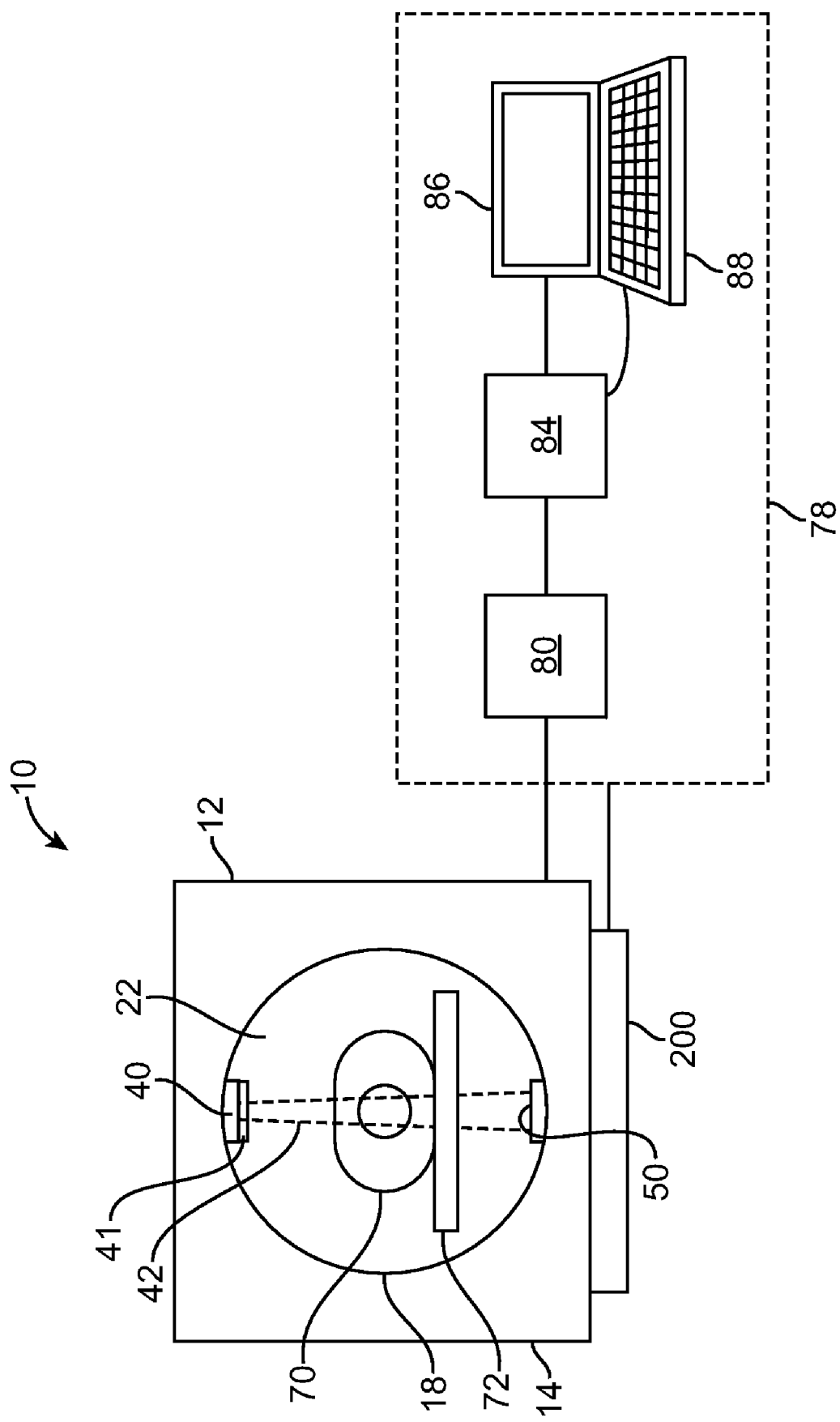
FIG. 1 illustrates a radiation system in accordance with some embodiments.

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments. Moreover, alternative configurations, components, methods, etc. discussed in conjunction with one embodiment can be used in any other embodiment even if such other embodiment does not discuss such alternatives or discusses different alternatives.

Figure 2:
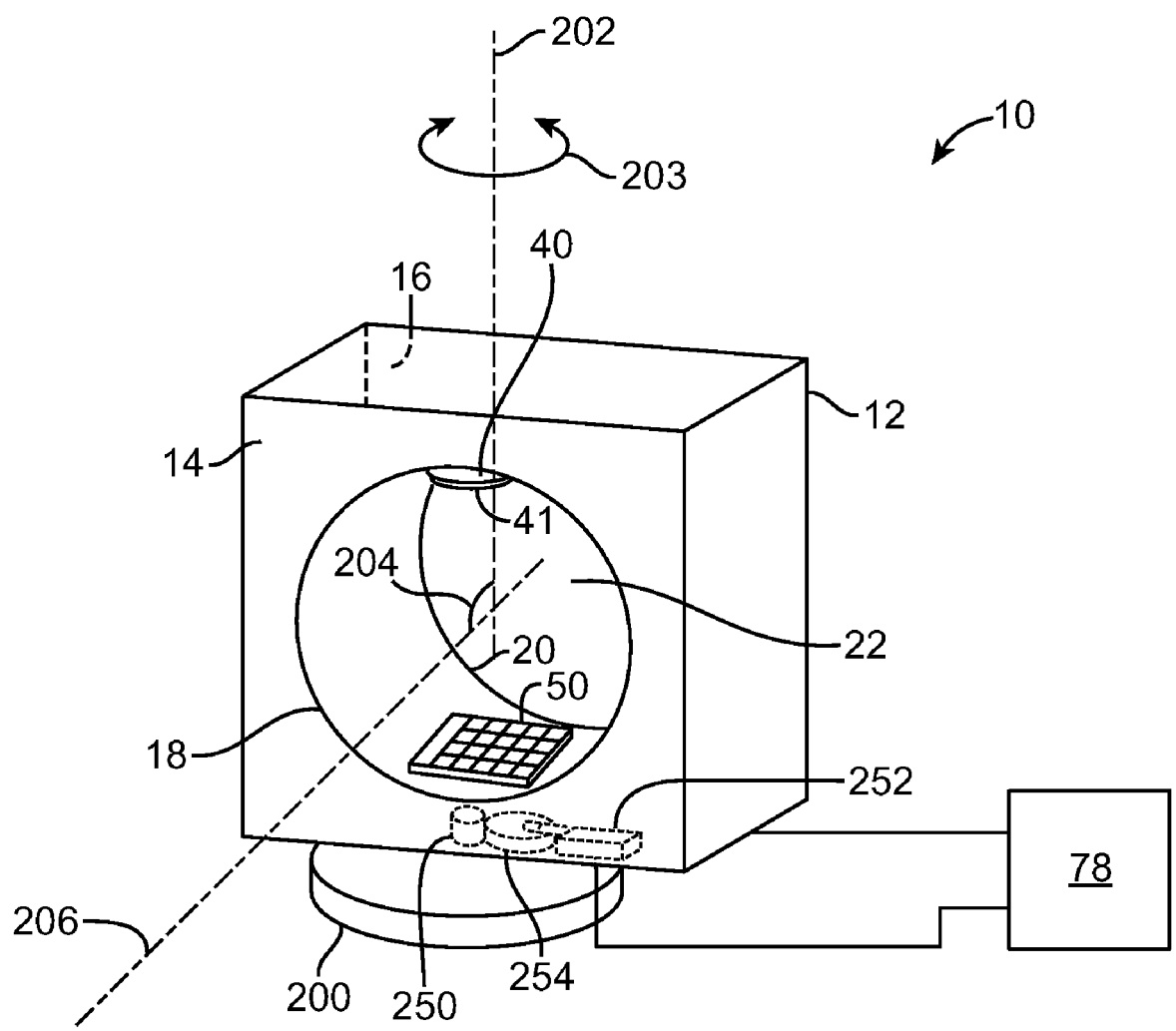
FIG. 2 illustrates an isometric view of the radiation system of FIG. 1.

FIGS. 1 and 2 illustrate a radiation system 10 in accordance with some embodiments. The radiation system 10 includes a structure 12 having a first side 14, a second side 16, a first opening 18 located on the first side 14, a second opening 20 located on the second side 16, and a bore 22 extending between the first and second openings 18, 20. In the illustrated embodiments, the openings 18, 20 are circular in shape and are sized for accommodating at least a part of a patient. In other embodiments, the openings 18, 20 can have other shapes. The bore 22 preferably has a cross sectional width that is wider than a patient's upper body (e.g., the shoulder), thereby allowing at least a top part of the patient to pass therethrough. For example, the bore 22 may have a width that is at least 24 inches, and more preferably, at least 30 inches. Alternatively, the bore 22 may have other sizes.

The through bore 22 of the structure 12 provides a passage for allowing at least a portion of a patient 70 (supported on a patient support 72) to be transported from one side of the structure 12 to an opposite side of the structure 12. The transportation of the patient from one side of the structure 12 to the opposite side may be performed before a treatment procedure, during a treatment procedure, and/or after a treatment procedure. For example, in some embodiments, a diagnostic procedure, such as an imaging procedure, may be performed (e.g., using the system 10 if the system 10 has imaging capability) on the patient (e.g., for the purpose of obtaining information, such as a position of a target region, of the patient), and the patient is then transported through the bore 22 to the opposite side of the structure 12 for a treatment procedure. In other embodiments, the patient is treated first (e.g., using the system 10 if the system 10 has treatment capability), and is then transported through the bore 22 to the opposite side of the structure 12 for further procedure(s), such as a diagnostic procedure (e.g., to evaluate a treatment procedure, or to verify location, orientation, and/or shape of a target tissue,), a treatment plan determination procedure, or a treatment procedure. In other embodiments, the structure 12 does not have the second opening 20, and the bore 22 does not extend through the structure 12.

It should be noted that the shape and configuration of the structure 12 should not be limited to the examples discussed previously, and that the structure 12 can have other configurations in other embodiments. For example, in other embodiments, the structure 12 can have a curvilinear shape, e.g., a circular perimeter, a donut shape, or other shapes. Also, in some embodiments, the structure 12 can have a size and shape such that the structure can house mechanical and electrical components associated with an operation of the radiation system 10 as desired. In such cases, the structure 12 functions as a housing. One advantage of such housing is that it prevents an object, such as a patient support, from colliding with a moving component (such as the radiation source 40 and/or the imager 50 described below) of the radiation system 10.

The radiation system 10 also includes a radiation source 40 for delivering a radiation beam 42. The radiation beam 42 can be a pencil beam, a fan beam, a cone beam, or other types of beams having different configurations. As used in this specification, the term "radiation source" refers to an emission point/region of a radiation beam (e.g., radiation beam 42), and may or may not include components, such as a particle generator, an accelerator, a cooling system, a shielding, etc., that are used to generate the radiation beam 42.

In the illustrated embodiments, the radiation source 40 is a treatment radiation source for providing treatment energy. In such cases, the radiation system 10 further includes one or more collimators 41 for controlling a delivery of the radiation beam 42 (e.g., changing a shape of the beam 42). A collimator can be, for example, a multi-leaf collimator, which is known in the art. The system 10 may also optionally include a beam stopper located opposite to the radiation source 40 to prevent or limit radiation passing into the environment. Alternatively, the radiation source 40 can be a diagnostic radiation source for providing diagnostic energy. In some embodiments, the treatment energy is generally those energies of 160 keV or greater, and more typically 1 MeV or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. For example, a radiation beam having an energy level that is typically used for treatment purpose may be considered as having a diagnostic energy level if the radiation beam is used for diagnostic purpose (e.g., for imaging). As such, the term "treatment energy" and the term "diagnostic energy" should not be limited to energy levels having certain magnitudes. In further embodiments, the first radiation source 40 is a multi-energy x-ray source that is capable of providing radiation energy at different energy levels. By way of example, the first radiation source 40 is able to generate X-ray radiation at a plurality of photon energy levels within a range anywhere between approximately 10 kilo-electron-volts (keV) and approximately 20 mega-electron-volts (MeV). Radiation sources capable of generating X-ray radiation at different energy levels are described in U.S. Pat. No. 6,888,919 B2, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003, both of which are expressly incorporated by reference in their entirety.

In the illustrated embodiments, the radiation source 40 is rotatably secured to the structure 12. For example, the radiation source 40 may be secured to a ring (which may be a full ring or a partial ring) that is rotatable relative to the structure 12 in a slip-ring configuration. In such cases, at least some of the components that are used to generate the radiation beam 42 may be disposed within the structure 12.

In the illustrated embodiments, the radiation system 10 further includes a control system 78. The control system 78 includes a processor 84, such as a computer processor, coupled to a control 80. The control system 78 may also include a monitor 86 for displaying data and an input device 88, such as a keyboard or a mouse, for inputting data. In some embodiments, during an operation of the radiation system 10, the radiation source 40 rotates about the patient (e.g., as in an arc-therapy). The rotation and the operation of the radiation source 40 are controlled by the control 80, which provides power and timing signals to the radiation source 40 and controls a rotational speed and position of the radiation source 40 based on signals received from the processor 84. Although the control 80 is shown as a separate component from the structure 12 and the processor 84, in alternative embodiments, the control 80 can be a part of the structure 12 or the processor 84.

As shown in FIG. 1, the radiation system 10 further includes an imager 50 located next to the first opening 18 and opposite from the radiation source 40. In some embodiments, the imager 50 includes a conversion layer made from a scintillator element, such as Cesium Iodide (CsI), and a photo detector array (e.g., a photodiode layer) coupled to the conversion layer. The conversion layer generates light photons in response to radiation, and the photo detector array, which includes a plurality of detector elements, is configured to generate electrical signal in response to the light photons from the conversion layer. The imager 50 can have a curvilinear surface (e.g., a partial circular arc). Such configuration is beneficial in that each of the imaging elements of the imager 50 is located substantially the same distance from the radiation source 40. In an alternative embodiment, the imager 50 may have a rectilinear surface or a surface having other profiles. The imager 50 can be made from amorphous silicon, crystal and silicon wafers, crystal and silicon substrate, or flexible substrate (e.g., plastic), and may be constructed using flat panel technologies or other techniques known in the art of making imaging device. In alternative embodiments, the imager 50 may use different detection schemes. For example, in alternative embodiments, instead of having the conversion layer, the imager 50 may include a photoconductor, which generates electron-hole-pairs or charges in response to radiation.

It should be noted that the configuration of the imager 50 should not be limited to the examples discussed previously, and that imagers having other configurations may be used in other embodiments. By way of example, U.S. patent application Ser. No. 10/439,350, entitled "MULTI ENERGY X-RAY IMAGER" filed on May 15, 2003, discloses imaging devices capable of generating signals in response to multiple radiation energy levels, and can be used as the imager 50 in accordance with some embodiments. In addition, U.S. patent application Ser. No. 10/013,199, entitled "X-RAY IMAGE ACQUISITION APPARATUS," and filed on Nov. 2, 2001, discloses an image detecting device that is capable of detecting multiple energy level X-ray images, and can also be used as the imager 50 in accordance with other embodiments. U.S. patent application Ser. No. 10/687,552, entitled "MULTI-ENERGY RADIATION DETECTOR," and filed on Oct. 15, 2003, discloses multi-energy radiation detectors that can be used as the imager 50 in different embodiments. In other embodiments, the imager 50 can be implemented using flat panel technologies. Also, in further embodiments, the imager 50 can be a multi-slice flat panel. Multi-slice flat panel CT has been described in U.S. patent application Ser. No. 10/687,552, entitled "MULTI-SLICE FLAT PANEL COMPUTED TOMOGRAPHY," and filed on Oct. 15, 2003. U.S. patent application Ser. Nos. 10/439,350, 10/013,199, and 10/687,550 are expressly incorporated by reference in their entirety. In other embodiments, the imager 50 may be similarly incorporated in any of the radiation systems 10 described herein.

The imager 50 may be used for a variety of purposes, depending on the configuration of the radiation system 10. For example, if the radiation source 40 is capable of delivering radiation having an energy level suitable for treatment purpose, then the imager 50 may be used to obtain dose information resulted from a delivery of treatment radiation by the radiation source 40. In other embodiments, if the radiation source 40 is capable of delivering radiation having an energy level suitable for imaging purpose, the imager 50 may also be used to obtain information, e.g., position, size, shape, and orientation, of a target. In further embodiments, the imager 50 is optional, and the radiation system 10 does not include the imager 50.

As shown in FIGS. 1 and 2, the structure 12 is rotatably secured to a support 200 such that the structure 12 can rotate (tilt) relative to the support 200 about an axis 202, as represented by arrow 203. Such configuration allows the radiation source 40 to be tilted about the axis 202 by rotating the structure 12 about the axis 202. As shown in the figure, the axis 202 forms an angle 204 with the axis 206 of the bore 22, wherein the angle 204 is a value that is approximately 90° (e.g., 90°±15°). In other embodiments, angle 204 may have other non-zero values. For example, the angle 204 may be more than 105° or less than 75°. In some cases, the axis 202 may be substantially vertical (e.g., the axis 202 forms an angle with a floor that is a value between 80° and 100°, such as 90°). In the illustrated embodiments, the support 200 is a base located below the structure 12. The base may be a platform that is secured to a floor, or alternatively, the floor itself. In other embodiments, the support 200 may have a frame configuration, and may be located at other positions relative to the structure 12. For example, in other embodiments, the support 200 may be a frame having two columns and a beam extending therebetween. In such cases, the structure 12 may be hanged below the beam, and is rotatably secured to the beam of the frame.

In the illustrated embodiments, the structure 12 is rotatably coupled to the support 200 via a bearing 250. The system 10 also include a motor 252 for driving a gear 254 to thereby rotate the structure 12. The motor 252 is connected to the control system 78, which controls a rotation of the structure 12 about the axis 202. In other embodiments, the motor 252 may be connected to a separate control system (not shown), such as a computer, which controls an operation of the motor 252 to thereby rotate the structure 12 relative to the support 200. In other embodiments, instead of a motor 252, the system 10 may include other types of mechanical system and/or linkage for rotating the structure 12 about the support 200. Also, in further embodiments, the system 10 may not include the motor 252 and the gear 254. In such cases, the rotation of the structure 12 about the axis 202 may be performed manually by an operator.

In some embodiments, the radiation system 10 may further include a support frame (not shown) to which an uppermost portion of the structure 12 is rotatably coupled via another bearing. In such cases, the structure 12 may be rotated about the axis 202 via the two bearings (one near the base, and another near the top of the structure 12).

Figure 3:
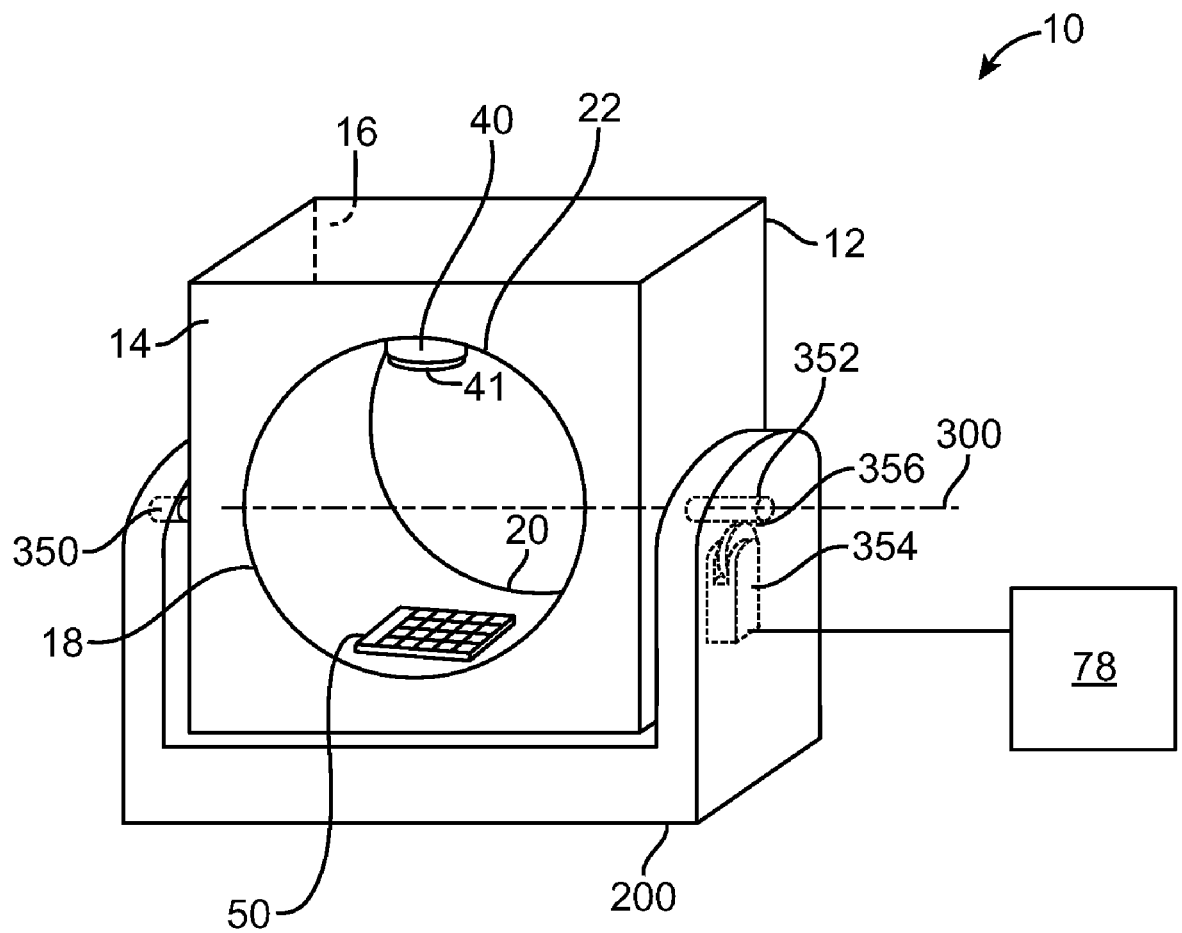
FIG. 3 illustrates an isometric view of a variation of the radiation system of FIG. 1 in accordance with other embodiments.

FIG. 3 illustrates a variation of the radiation system 10 in accordance with other embodiments. The radiation system 10 is similar to the radiation system described with reference to FIGS. 1 and 2, except that the structure 12 is rotatable (tiltable) relative to the support 200 about an axis 300 that is approximately horizontal (e.g., the axis 300 forms an acute angle with a floor that is less than 15°, such as 0°). In such cases, the structure 12 may be tilted about the axis 300 to thereby tilt the radiation source 40 about the axis 300.

In the illustrated embodiments, the structure 12 is rotatably coupled to the support 300 via bearings 350, 352. The bearing 350 is located adjacent to a left side of the structure 12 (e.g., a location towards a left of a center of the structure 12), and the bearing 352 is located adjacent to a right side of the structure 12 (e.g., a location towards a right of a center of the structure 12). The system 10 also includes a motor 354 for driving a gear 356 to thereby rotate the structure 12. The motor 354 is connected to the control system 78, which controls a rotation of the structure 12 about the axis 300. In other embodiments, the motor 354 may be connected to a separate control system (not shown), such as a computer, which controls an operation of the motor 354 to thereby rotate the structure 12 relative to the support 200. In other embodiments, instead of a motor 354, the system 10 may include other types of mechanical system and/or linkage for rotating the structure 12 about the support 200. Also, in further embodiments, the system 10 may not include the motor 354 and the gear 356. In such cases, the rotation of the structure 12 about the axis 300 may be performed manually by an operator.

Figure 4:
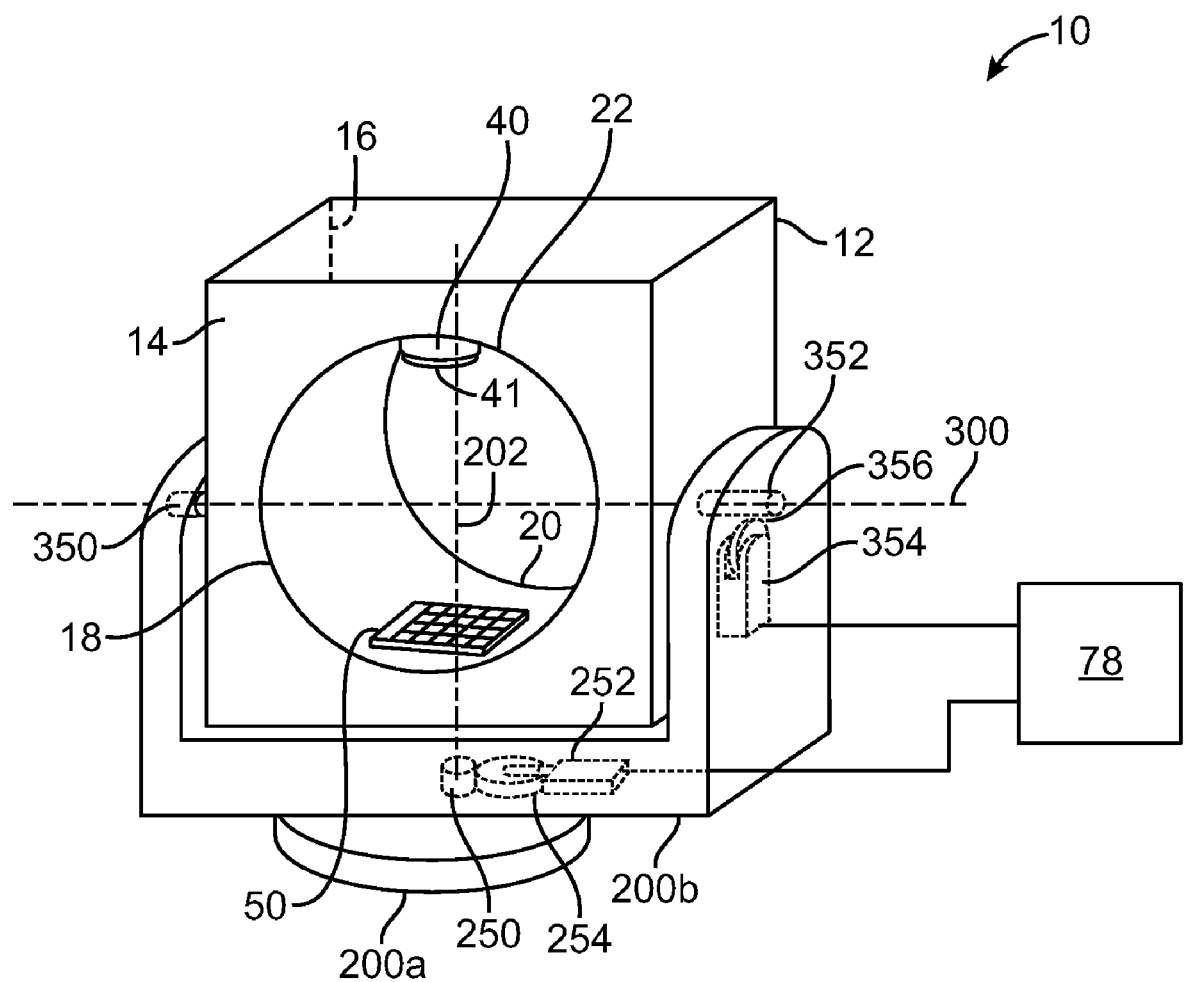
FIG. 4 illustrates an isometric view of a variation of the radiation system of FIG. 1 in accordance with other embodiments.

In the above embodiments, the structure 12 is configured to rotate about a single axis (e.g., axis 202 or 300). However, in other embodiments, the structure 12 may be configured to rotate about a plurality of axes (e.g., two or more axes). FIG. 4 illustrates a variation of the radiation system 10 in accordance with other embodiments. The radiation system 10 is similar to the radiation system described with reference to FIGS. 1-3, except that the structure 12 is rotatable (tiltable) relative to a first support 200a about a first axis 202, and is rotatable (tiltable) relative to a second support 200b about a second axis 300. In such cases, the structure 12 may be tilted about the first axis 202 to thereby tilt the radiation source 40 about the first axis 202 and/or about the second axis 300 to thereby tilt the radiation source 40 about the second axis 300. In the illustrated embodiments, the first axis 202 is approximately vertical (e.g., the axis 202 forming an angle with a floor that is a value between 80° and 100°), and the second axis 300 is approximately horizontal (e.g., the axis 300 forming an acute angle with a floor that is less than 15°, such as 0°). In other embodiments, the first and second axes 202, 300 may have other orientations. Also, in further embodiments, the system 10 of FIG. 4 may further include the motor 252 for rotating the structure 12 about the first axis 202, and/or the motor 354 for rotating the structure about the second axis 300.

In any of the embodiments described herein, the tilting of the structure 12 (and therefore the radiation source 40) may be performed during a patient setup session (e.g., before a treatment or imaging procedure). For example, the structure 12 may be rotated about the axis 202 and/or the axis 300 to thereby place the radiation source 40 at a desired position and orientation relative to a patient. The desired position and orientation may be prescribed by a treatment plan. After the structure 12 has been desirably positioned, the radiation source 40 may then be used to deliver treatment radiation beam to treat the patient in accordance with a treatment plan (if the radiation source 40 is capable of delivering treatment radiation). Alternatively, the radiation source 40 may be used to deliver diagnostic radiation beam to image a portion of the patient (if the radiation source 40 is capable of delivering diagnostic radiation).

In other embodiments, in addition to, or instead of, tilting the structure 12 during a patient setup, the tilting of the structure 12 (and therefore the radiation source 40) may be performed during a treatment procedure if the radiation source 40 is capable of providing treatment radiation beam. For example, the tilting of the structure 12 may be performed in between radiation delivery sessions during a treatment procedure, or alternatively, while the radiation source 40 is delivering radiation. In some embodiments, the rotation of the radiation source 40 relative to the structure 12, and the rotation of the structure 12 about the axis 202 and/or the axis 300, may be carried out to direct the treatment beam along a path prescribed by a treatment plan. In further embodiments, the collimator may also be operated in conjunction with the movement of the radiation source 40 and/or the structure 12, to thereby direct a beam towards a target. For example, leafs of the collimator may be positioned to thereby assist aiming of a beam towards a target. In further embodiments, leafs of the collimator may be positioned in conjunction with movement of the radiation source 40 and/or the structure 12 to perform intensity modulated radiation therapy (IMRT). In IMRT, leafs of a multi-leaf collimator move to cause one region of a target to receive more radiation than another region of the target. In other embodiments, leafs of the multi-leaf collimator may be positioned to simultaneously perform both IMRT and tracking of the target.

As shown in the illustrated embodiments, configuring the structure 12 to rotate about the axis 202 and/or the axis 300 is advantageous in that it allows accommodation of various positions of the patient. For example, in some embodiments, the structure 12 may rotate about the axis 300 to accommodate a patient that is standing up, sitting up, or resting on an inclined patient support. In some cases, the patient support 72 supporting the patient may be inclined, and the structure 12 may be rotated about the axis 300 such that the plane of the opening 18 is approximately perpendicular to the longitudinal axis of the patient support 72. Such configuration allows image slices that are perpendicular to the longitudinal axis of the support 72 to be obtained in a conventional manner, while the patient support 72 is inclined. In other embodiments, the plane of the opening 18 may not be perpendicular to the longitudinal axis of the patient support 72.

Also, unlike existing systems which generate image slices that are perpendicular to the z-axis (i.e., longitudinal axis) of a patient support, the system 10 allows one or more image slices that are non-perpendicular to the z-axis to be obtained by rotating the structure 12 about the axis 202 and/or the axis 300 such that the axis 206 of the bore 22 forms an angle with the z-axis of the patient support. In addition, the system 10 is advantageous in that it allows more different configurations of treatment plans to be implemented. For example, by rotating the structure 12 about the axis 300, the radiation source 40 may deliver radiation beams (e.g., treatment beam) from different angles relative to a vertical plane towards the patient. Also, in the case of arc-therapy, the plane formed by the treatment beams (from different arc-positions of the radiation source 40 relative to the structure 12) may be at an angle relative to a coronal or sagittal plane of the patient. Furthermore, the rotational movement(s) of the structure 12 may be used to correct angular positioning of the treatment beam relative to a target. Such may be accomplished before a treatment procedure, or during a treatment procedure.

Figure 5:
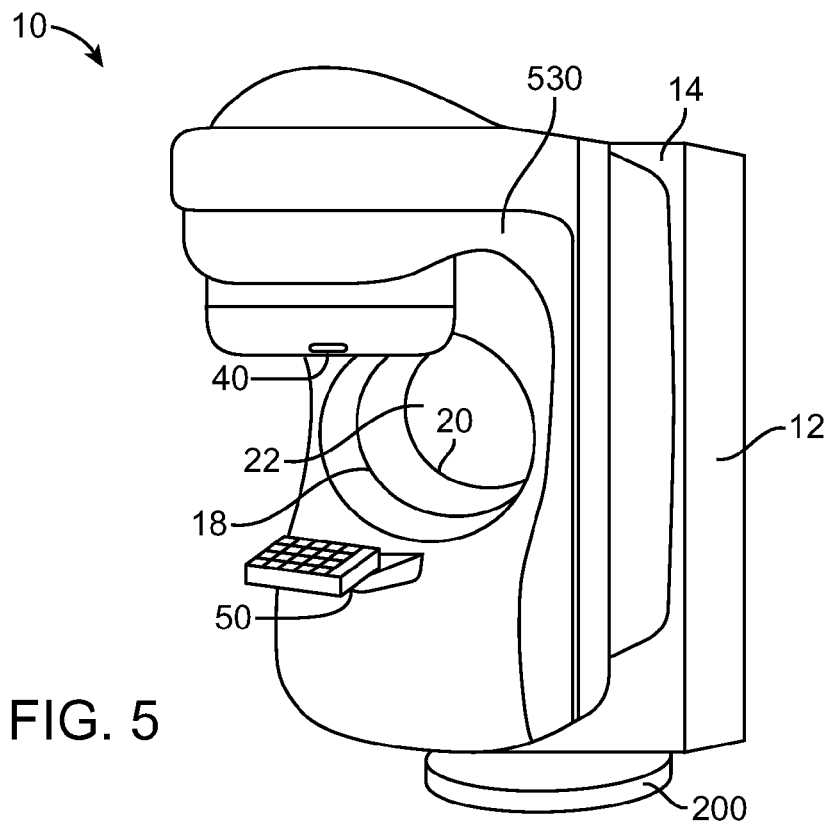
FIG. 5 illustrates an isometric view of a radiation system in accordance with other embodiments.

It should be noted that the radiation system 10 should not be limited to the configuration discussed previously, and that the radiation system 10 can have other configurations in other embodiments. For example, in some embodiments, the radiation system 10 can have the configuration shown in FIG. 5. In the illustrated embodiments, the radiation system 10 includes the structure 12, which has a configuration that is similar to that discussed previously with reference to structure 12 of FIG. 1. The radiation system 10 also includes an arm 530 to which the radiation source 40 is secured. Some or all of the components used to generate the radiation beam can be housed within the arm 530, the structure 12, a separate housing (not shown), or combination thereof. The arm 530 may be fixedly secured to the structure 12, or alternatively, be rotatably secured to the structure 12. The arm 530 of the radiation system 10 is advantageous in that it allows radiation be delivered to a portion of a patient that is placed outside the bore 22. In particular, since the patient is not confined by the bore 22, the patient can be oriented at different angles relative to the axis 206 outside the bore 22. For example, the patient can be positioned at least partially outside the bore 22 and oriented at an angle relative to the axis 206.

Figure 6B:
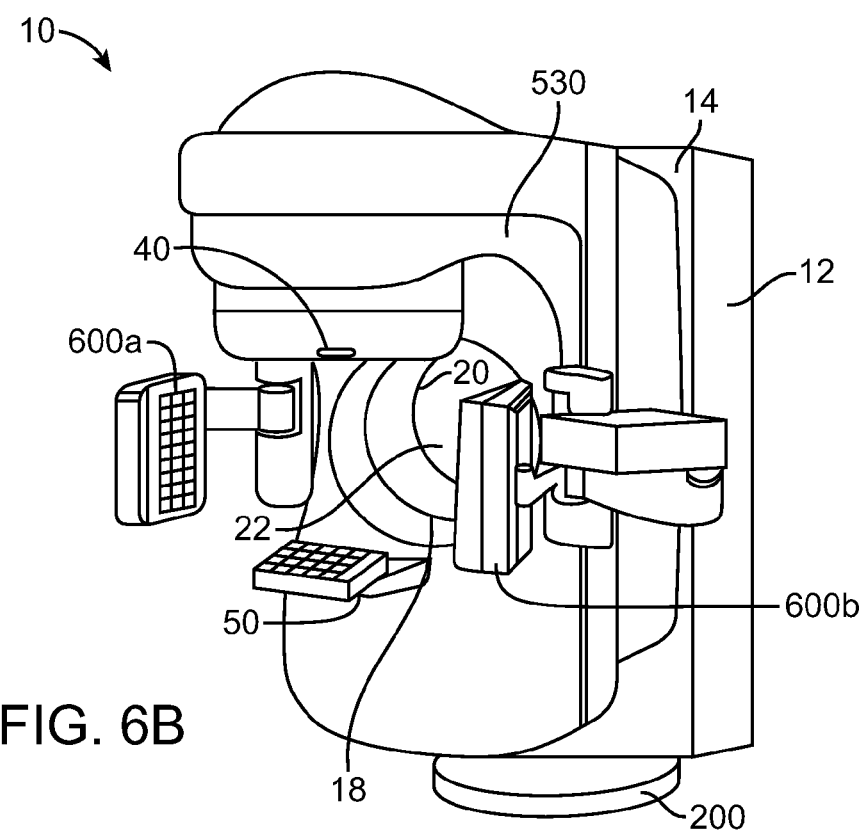
FIG. 6B illustrates a variation of the radiation system of FIG. 5 in accordance with other embodiments, showing the system having two PET imagers.
Figure 6A:
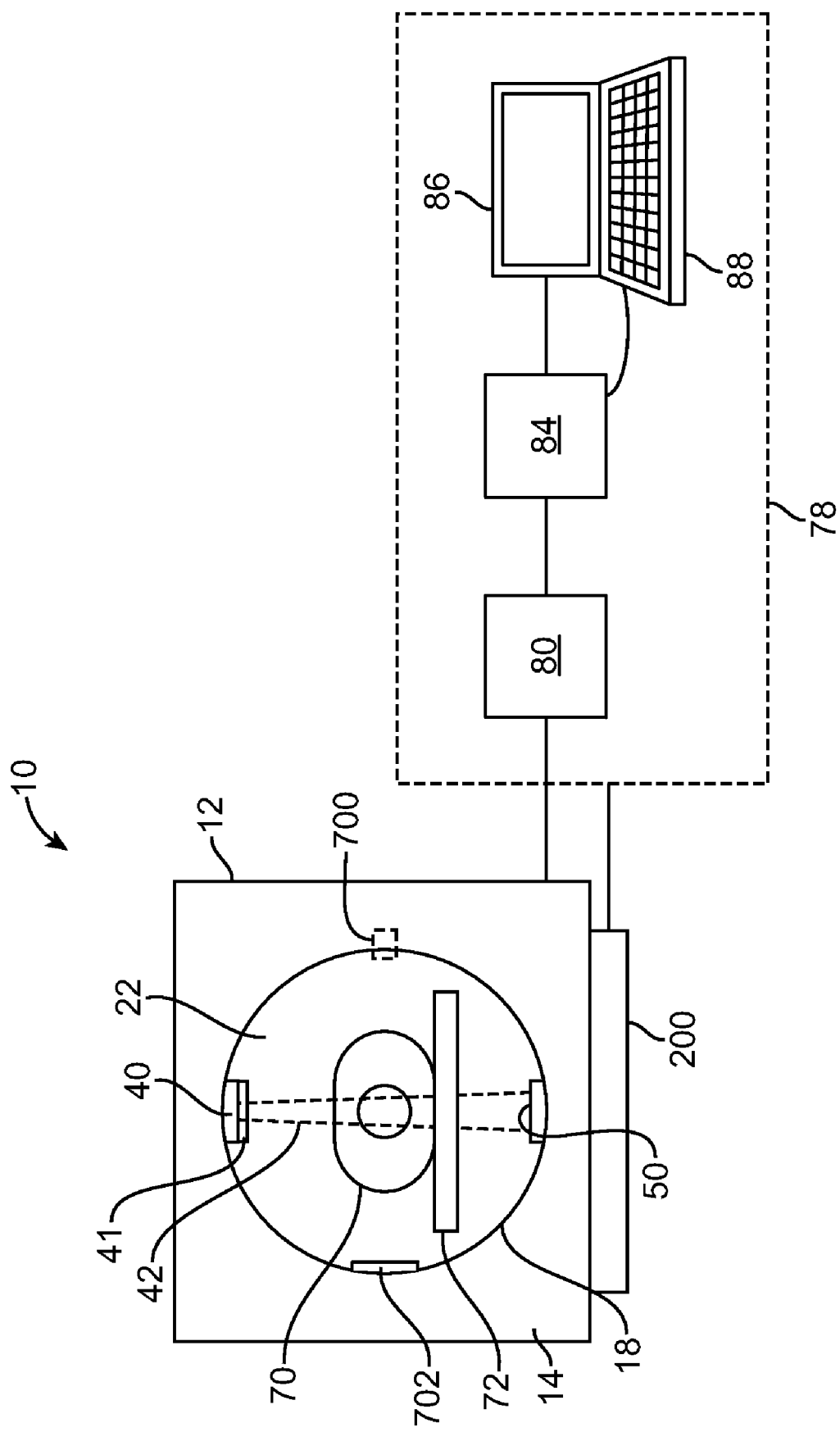
FIG. 6A illustrates a variation of the radiation system of FIG. 1 in accordance with other embodiments, showing the system having a x-ray tube and imager.

In some embodiments, any of the radiation systems 10 described herein can further include a x-ray source, such as tube 700 and an imager 702 secured adjacent to the radiation source 40 (FIG. 6A). The x-ray tube 700 and the imager 702 are configured to image at least a portion of the patient. The x-ray tube 700 and the imager 702 can be used to generate data regarding a patient while the patient is positioned in an operative position associated with the radiation source 40. For example, in some embodiments, the x-ray tube 700 generates a cone beam, and the imager 702 generates cone beam CT data, which represent image of a portion of a patient. In the illustrated embodiments, the x-ray tube 700 and the imager 702 are rotatably secured to the structure 12 (e.g., the x-ray tube 700 and the imager 702 may be secured to a ring that is rotatable relative to the structure 12). In other embodiments, the x-ray tube 700 and the imager 702 may be fixedly secured to the structure 12, and may be secured to other parts of the structure 12. In further embodiments, instead of including one x-ray tube 700 and imager 702, the radiation system 10 may include a plurality of diagnostic radiation sources (e.g., x-ray tubes) and a plurality of diagnostic imagers. The diagnostic radiation sources may be ones that generate keV radiation, and the diagnostic imagers may be ones that are configured to receive keV radiation. For examples, in some embodiments, the system 10 can further include two diagnostic radiation sources that deliver keV radiation, and two respective imagers that operate with the corresponding two diagnostic radiation sources. Such system can be used for stereoscopic imaging. Alternatively, the diagnostic radiation sources and the imagers may be configured to respectively generate and receive radiation at other energy levels.

In other embodiments, other types of diagnostic devices, such as a laminar tomography device, a MRI device, a fluoroscope, an angiography device, a PET device, a SPECT device, a PET-CT device, a tomosynthesis imaging device, a CT device, a CBCT device, etc. can be used/included with the radiation system 10. For example, the system 10 of FIG. 5 may further includes two PET imagers 600a, 600b (FIG. 6B). Any of these diagnostic devices may be used to obtain positioning information of a target. In some embodiments, the processor 84 receives such positioning information, and position the radiation source 40 and/or the structure 12 based on the positioning information, to thereby aim the treatment beam towards the target. In further embodiments, a plurality of diagnostic devices (e.g., any multiple, or any combination, of the diagnostic devices described) may be used/included with the radiation system 10.

In any of the embodiments described herein, the system 10 may include, or used with, a patient support (e.g., the patient support 702) that can translate in two or more directions. For example, in some embodiments, the patient support 702 may translate along the z-direction (its longitudinal axis), and along a y-direction (e.g., a lateral direction). In further embodiments, the patient support 702 may further translate along a third direction, e.g., in a vertical direction. In such cases, moving the patient support can provide corrective translations of the target. Patient supports capable of translating in a plurality of directions are described in U.S. patent application Ser. No. 11/415,974, entitled "Patient Support Systems," filed on May 1, 2006, the entire disclosure of which is expressly incorporated by reference herein.

Computer System Architecture

Figure 7:
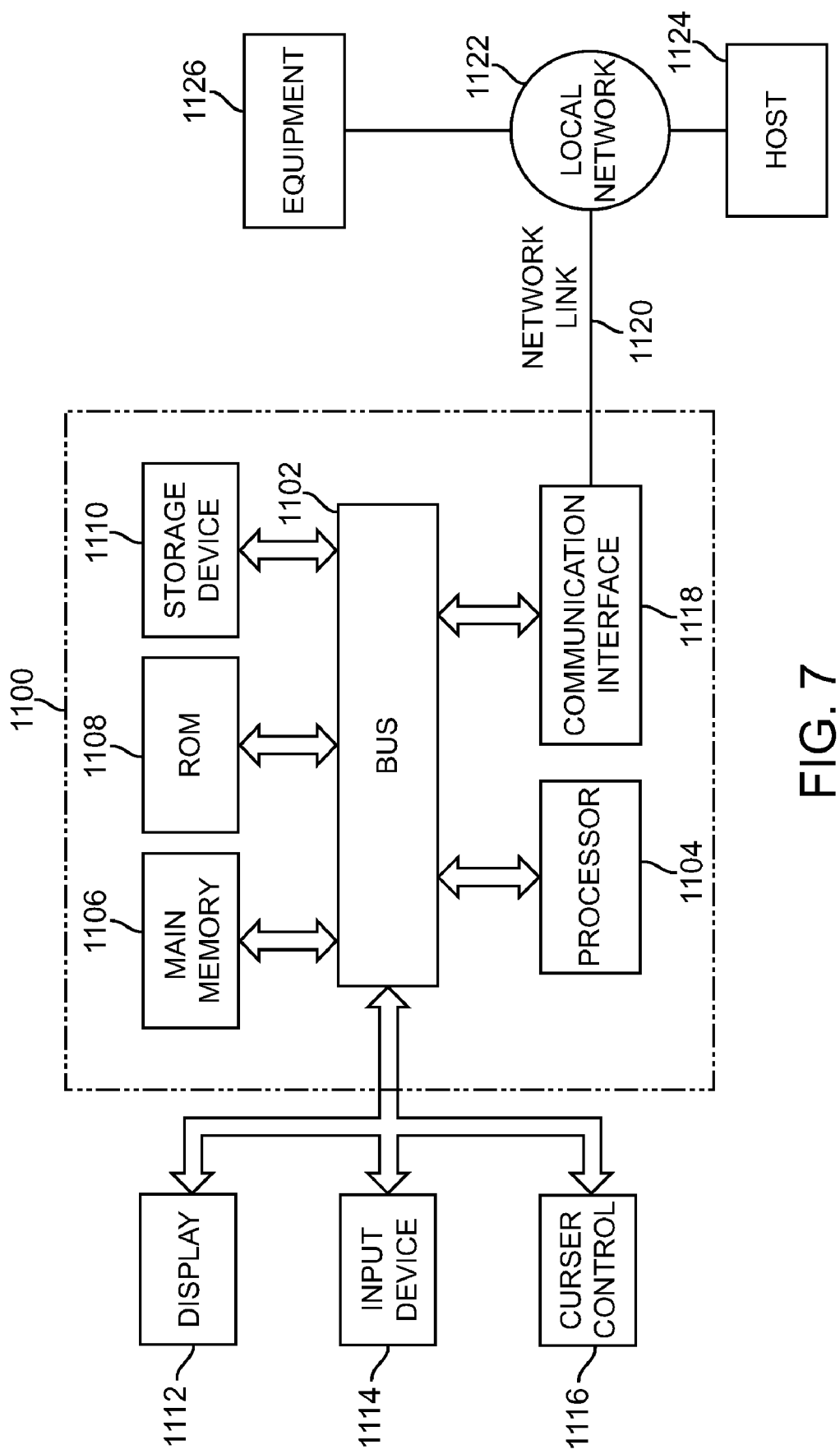
FIG. 7 illustrates a block diagram of a computer system that can be used to control an operation of a radiation system in accordance with some embodiments.

FIG. 7 is a block diagram illustrating an embodiment of a computer system 1100 that can be used to implement various embodiments of the method described herein. Computer system 1100 includes a bus 1102 or other communication mechanism for communicating information, and a processor 1104 coupled with the bus 1102 for processing information. The processor 1104 may be an example of the processor 114, or alternatively, an example of a component of the processor 114. The computer system 1100 also includes a main memory 1106, such as a random access memory (RAM) or other dynamic storage device, coupled to the bus 1102 for storing information and instructions to be executed by the processor 1104. The main memory 1106 also may be used for storing temporary variables or other intermediate information during execution of instructions to be executed by the processor 1104. The computer system 1100 further includes a read only memory (ROM) 1108 or other static storage device coupled to the bus 1102 for storing static information and instructions for the processor 1104. A data storage device 1110, such as a magnetic disk or optical disk, is provided and coupled to the bus 1102 for storing information and instructions.

The computer system 1100 may be coupled via the bus 1102 to a display 117, such as a cathode ray tube (CRT), or a flat panel display, for displaying information to a user. An input device 1114, including alphanumeric and other keys, is coupled to the bus 1102 for communicating information and command selections to processor 1104. Another type of user input device is cursor control 1116, such as a mouse, a trackball, or cursor direction keys for communicating direction information and command selections to processor 1104 and for controlling cursor movement on display 117. This input device typically has two degrees of freedom in two axes, a first axis (e.g., x) and a second axis (e.g., y), that allows the device to specify positions in a plane.

In some embodiments, the computer system 1100 can be used to perform various functions described herein. According to some embodiments of the invention, such use is provided by computer system 1100 in response to processor 1104 executing one or more sequences of one or more instructions contained in the main memory 1106. Those skilled in the art will know how to prepare such instructions based on the functions and methods described herein. Such instructions may be read into the main memory 1106 from another computer-readable medium, such as storage device 1110. Execution of the sequences of instructions contained in the main memory 1106 causes the processor 1104 to perform the process steps described herein. One or more processors in a multi-processing arrangement may also be employed to execute the sequences of instructions contained in the main memory 1106. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1104 for execution. Such a medium may take many forms, including but not limited to, non-volatile media, volatile media, and transmission media. Non-volatile media includes, for example, optical or magnetic disks, such as the storage device 1110. Volatile media includes dynamic memory, such as the main memory 1106. Transmission media includes coaxial cables, copper wire and fiber optics, including the wires that comprise the bus 1102. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1104 for execution. For example, the instructions may initially be carried on a magnetic disk of a remote computer. The remote computer can load the instructions into its dynamic memory and send the instructions over a telephone line using a modem. A modem local to the computer system 1100 can receive the data on the telephone line and use an infrared transmitter to convert the data to an infrared signal. An infrared detector coupled to the bus 1102 can receive the data carried in the infrared signal and place the data on the bus 1102. The bus 1102 carries the data to the main memory 1106, from which the processor 1104 retrieves and executes the instructions. The instructions received by the main memory 1106 may optionally be stored on the storage device 1110 either before or after execution by the processor 1104.

The computer system 1100 also includes a communication interface 1118 coupled to the bus 1102. The communication interface 1118 provides a two-way data communication coupling to a network link 1120 that is connected to a local network 1122. For example, the communication interface 1118 may be an integrated services digital network (ISDN) card or a modem to provide a data communication connection to a corresponding type of telephone line. As another example, the communication interface 1118 may be a local area network (LAN) card to provide a data communication connection to a compatible LAN. Wireless links may also be implemented. In any such implementation, the communication interface 1118 sends and receives electrical, electromagnetic or optical signals that carry data streams representing various types of information.

The network link 1120 typically provides data communication through one or more networks to other devices. For example, the network link 1120 may provide a connection through local network 1122 to a host computer 1124 or to equipment 1126, such as any of the devices herein (e.g., device 166, system 10, etc.), or a switch operatively coupled to any of the devices described herein. The data streams transported over the network link 1120 can comprise electrical, electromagnetic or optical signals. The signals through the various networks and the signals on the network link 1120 and through the communication interface 1118, which carry data to and from the computer system 1100, are exemplary forms of carrier waves transporting the information. The computer system 1100 can send messages and receive data, including program code, through the network(s), the network link 1120, and the communication interface 1118.

Although particular embodiments of the present inventions have been shown and described, it will be understood that it is not intended to limit the present inventions, and it will be obvious to those skilled in the art that various changes and modifications may be made without departing from the spirit and scope of the present inventions. For example, the term "image" or "image data" as used in this specification includes image data that may be stored in a circuitry or a computer-readable medium, and should not be limited to image data that is displayed visually. Also, it should be noted that in other embodiments, the radiation system 10 may not include one or more of the components described herein. In addition, in other embodiments, the radiation system 10 may include any of the components described herein, even if the components are described as separate elements from the radiation system 10. Further, the terms "first axis" and "second axis" should not be limited to those described with reference to FIG. 4, and may be used to refer to different axes in different embodiments. For example, the term "first axis" may be used to refer to an axis of the bore. Also, the term "second axis" may be used to refer to axis 300 or axis 202. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A radiation system, comprising:
    a gantry having an opening and a first axis associated with the opening, the opening having a width that is at least 24 inches;
    a radiation source coupled to the gantry;
    a first bearing located adjacent a left side of the gantry;
    a second bearing located adjacent a right side of the gantry; and
    an imager coupled to the gantry, wherein a first line extending from the imager to the first axis forms an angle with a second line extending from the radiation source to the first axis, the angle being a value that is less than 180°;
    wherein the gantry is tiltable about the first and second bearings, the first and second bearings forming a second axis that is at a first angle relative to the first axis.

2. The radiation system of claim 1, wherein the radiation source is capable of providing radiation suitable for treating at least a portion of a patient 3. The radiation system of claim 1, wherein the radiation source is capable of providing radiation suitable for imaging at least a portion of a patient.

4. The radiation system of claim 1, further comprising a collimator located adjacent to the radiation source.

5. The radiation system of claim 1, further comprising an additional radiation source, wherein the imager is in operative association with the additional radiation source.

6. The radiation system of claim 1, wherein the angle is a value that is between 80° and 100°.

7. The radiation system of claim 1, wherein the second axis is horizontal.

8. The radiation system of claim 1, further comprising a base to which the gantry is rotatably coupled, wherein the gantry is tiltable relative to the base about a third axis.

9. The radiation system of claim 8, wherein an uppermost portion of the gantry is not coupled to a support frame of the gantry.

10. The radiation system of claim 8, wherein the third axis is vertical.

11. The radiation system of claim 1, wherein the opening is wide enough to accommodate shoulders of a patient.

12. The radiation system of claim 1, further comprising a x-ray source in operative association with the imager.

13. The radiation system of claim 1, wherein the gantry comprises a ring gantry.

14. The radiation system of claim 1, wherein the gantry comprises a C-arm configuration.

15. The radiation system of claim 1, further comprising a processor configured to generate a signal to cause a tilting of the gantry in accordance with a treatment plan.

16. A radiation system, comprising:
a gantry having an opening and a first axis associated with the opening, the opening having a width that is at least 24 inches;
a radiation source coupled to the gantry, wherein the radiation source is capable of providing radiation suitable for treating at least a portion of a patient; and
a base to which the gantry is rotatably coupled, wherein the gantry is tiltable relative to the base about a second axis that forms an angle relative to the first axis;
wherein the gantry comprises a C-arm configuration.

17. The radiation system of claim 16, further comprising an imager in operative association with the radiation source.

18. The radiation system of claim 16, wherein the angle is a value that is between 80° and 100°.

19. The radiation system of claim 16, wherein the second axis is vertical.

20. The radiation system of claim 16, wherein the opening is wide enough to accommodate shoulders of a patient.

21. The radiation system of claim 16, further comprising a support frame, wherein the gantry is rotatably coupled to the support frame.

22. The radiation system of claim 16, wherein the radiation source is tiltable about a third axis that forms a second angle relative to the first axis.

23. The radiation system of claim 16, wherein the gantry is tiltable relative to the base about a third axis.

24. A radiation system, comprising:
a gantry having an opening and a first axis associated with the opening, the opening having a width that is at least 24 inches;
a radiation source coupled to the gantry;
a base to which the gantry is rotatably coupled, wherein the gantry is tiltable relative to the base about a second axis that forms an angle relative to the first axis; and
a collimator located adjacent to the radiation sources;
wherein the gantry comprises a C-arm configuration.

25. A radiation system, comprising:
a gantry having an opening and a first axis associated with the opening, the opening having a width that is at least 24 inches;
a radiation source coupled to the gantry;
a base to which the gantry is rotatably coupled, wherein the gantry is tiltable relative to the base about a second axis that forms an angle relative to the first axis;
an imager coupled to the gantry, wherein a first line extending from the imager to the first axis forms an angle with a second line extending from the radiation source to the first axis, the angle being a value that is less than 180°; and
a x-ray source in operative association with the imager;
wherein the gantry comprises a C-arm configuration.

26. A radiation system, comprising:
a gantry having an opening and a first axis associated with the opening;
a treatment radiation source coupled to the gantry;
a diagnostic radiation source coupled to the gantry; and
an imager in operative position relative to the diagnostic radiation source;
wherein the treatment radiation source tiltable about a second axis that forms a first angle relative to the first axis.

27. The radiation system of claim 26, wherein the second axis is horizontal.

28. The radiation system of claim 26, further comprising a first bearing located adjacent a left side of the gantry, and a second bearing located adjacent a right side of the gantry, the first and second bearings forming the second axis.

29. The radiation system of claim 26, wherein the second axis is vertical.

30. The radiation system of claim 26, further comprising a base to which the gantry is rotatably coupled, wherein the gantry has a C-arm configuration.

31. The radiation system of claim 26, wherein the treatment radiation source is also tiltable about a third axis that forms a second angle relative to the first axis.

32. The radiation system of claim 31, wherein the second axis is horizontal and the first axis is vertical.

33. The radiation system of claim 26, wherein a first line extending from the imager to the first axis forms an angle with a second line extending from the treatment radiation source to the first axis, the angle being a value that is less than 180°.

34. A radiation system, comprising:
a gantry having an opening and a first axis associated with the opening, the opening having a width that is at least 24 inches;
a radiation source coupled to the gantry;
a first bearing located adjacent a left side of the gantry;
a second bearing located adjacent a right side of the gantry;
a collimator located adjacent to the radiation source; and
an imager coupled to the gantry;
wherein the gantry is tiltable about the first and second bearings, the first and second bearings forming a second axis that is at a first angle relative to the first axis; and
wherein the radiation source is tiltable about a third axis that forms a second angle relative to the first axis.

35. The radiation system of claim 34, wherein a first line extending from the imager to the first axis forms an angle with a second line extending from the radiation source to the first axis, the angle being a value that is less than 180°.

36. The radiation system of claim 34, wherein the gantry comprises a C-arm configuration.

37. A radiation system, comprising:
a gantry having an opening and a first axis associated with the opening, the opening having a width that is at least 24 inches;
a radiation source coupled to the gantry;
a first bearing located adjacent a left side of the gantry;
a second bearing located adjacent a right side of the gantry; and
an imager coupled to the gantry, wherein a first line extending from the imager to the first axis forms an angle with a second line extending from the radiation source to the first axis, the angle being a value that is less than 180°;
wherein the gantry is tiltable about the first and second bearings, the first and second bearings forming a second axis that is at a first angle relative to the first axis; and
wherein the radiation source is tiltable about a third axis that forms a second angle relative to the first axis.

38. The radiation system of claim 37, further comprising a collimator located adjacent to the radiation source.

39. The radiation system of claim 37, further comprising an additional radiation source, wherein the imager is in operative association with the additional radiation source.

40. A radiation system, comprising:
a gantry having an opening and a first axis associated with the opening, the opening having a width that is at least 24 inches, wherein the gantry comprises a C-arm configuration;
a radiation source coupled to the gantry;
a first bearing located adjacent a left side of the gantry;

a second bearing located adjacent a right side of the gantry;
wherein the gantry is tiltable about the first and second bearings, the first and second bearings forming a second axis that is at a first angle relative to the first axis; and
wherein the radiation source is tiltable about a third axis that forms a second angle relative to the first axis.

41. The radiation system of claim 40, further comprising a collimator located adjacent to the radiation source.

42. The radiation system of claim 40, further comprising an imager, wherein a first line extending from the imager to the first axis forms an angle with a second line extending from the radiation source to the first axis, the angle being a value that is less than 180°.

* * * * *